(12) United States Patent
Gilbert et al.

(10) Patent No.: US 8,211,042 B2
(45) Date of Patent: Jul. 3, 2012

(54) HIGH TORQUE ACTIVE MECHANISM FOR ORTHOTIC AND/OR PROSTHETIC DEVICES

(75) Inventors: Benoit Gilbert, Lac Beauport (CA); David Landry, Saint-Chrysostome (CA)

(73) Assignee: Victom Human Bionics Inc., Saint-Augustin-De-Desmaures, Quebec (CA)

( * ) Notice: Subject to any disclaimer, the term of this patent is extended or adjusted under 35 U.S.C. 154(b) by 404 days.

(21) Appl. No.: 12/160,736

(22) PCT Filed: Jan. 7, 2008

(86) PCT No.: PCT/CA2008/000012
§ 371 (c)(1),
(2), (4) Date: May 12, 2009

(87) PCT Pub. No.: WO2008/080232
PCT Pub. Date: Jul. 10, 2008

(65) Prior Publication Data
US 2010/0160844 A1    Jun. 24, 2010

Related U.S. Application Data

(60) Provisional application No. 60/878,689, filed on Jan. 5, 2007.

(51) Int. Cl.
*A61F 5/00* (2006.01)
*A61F 2/64* (2006.01)
(52) U.S. Cl. ............... 602/16; 602/26; 623/43; 623/45
(58) Field of Classification Search ........... 602/5, 16, 602/23, 24, 25, 26, 27, 28, 29, 61, 62; 601/5; 623/43, 44, 45, 18.11
See application file for complete search history.

(56) References Cited

U.S. PATENT DOCUMENTS

| 4,030,141 A | 6/1977 | Graupe |
| 4,179,759 A | 12/1979 | Smith |
| 4,521,924 A | 6/1985 | Jacobsen et al. |

(Continued)

FOREIGN PATENT DOCUMENTS

CN    2400072 Y    10/2000

(Continued)

OTHER PUBLICATIONS

Dietl, H., Der Einsatz von Elektronik bei Prothesen zur Versorgung der unteren Extremitat, Med. Orth. Tech 117 (1997)31-35.

(Continued)

*Primary Examiner* — Michael Brown
*Assistant Examiner* — Ophelia Hawthorne
(74) *Attorney, Agent, or Firm* — Knobbe, Martens, Olson & Bear LLP (57) ABSTRACT

A high torque active mechanism for an orthotic and/or prosthetic joint using a primary brake which can be provide by magnetorheological (MR) rotational damper incorporating and an additional friction brake mechanism driven by the braking force generated by the MR damper. This combination of MR damper and friction brake mechanism allows an increase in torque density while keeping the same level of motion control offered by the MR damper alone. The increased torque density achieved by this high torque active mechanism allows to minimize the size of the actuating system, i.e. its diameter and/or breath, while maximizing its braking torque capability. In this regard, the friction brake mechanism is advantageously positioned around the MR damper, such that the dimension of the package is minimized.

32 Claims, 9 Drawing Sheets

U.S. PATENT DOCUMENTS

| | | |
|---|---|---|
| 4,558,704 A | 12/1985 | Petrofsky |
| 4,617,920 A | 10/1986 | Carsalade |
| 4,865,024 A | 9/1989 | Hensley et al. |
| 4,994,086 A | 2/1991 | Edwards |
| 5,062,856 A | 11/1991 | Sawamura et al. |
| 5,062,857 A | 11/1991 | Berringer |
| 5,133,773 A | 7/1992 | Sawamura et al. |
| 5,133,774 A | 7/1992 | Sawamura et al. |
| 5,174,168 A | 12/1992 | Takagi et al. |
| 5,201,772 A | 4/1993 | Maxwell |
| 5,246,465 A | 9/1993 | Rincoe et al. |
| 5,252,102 A | 10/1993 | Singer et al. |
| 5,383,939 A | 1/1995 | James |
| 5,443,528 A | 8/1995 | Allen |
| 5,476,441 A | 12/1995 | Durfee et al. |
| 5,571,205 A | 11/1996 | James |
| 5,571,213 A | 11/1996 | Allen |
| 5,650,704 A | 7/1997 | Pratt et al. |
| 5,704,946 A | 1/1998 | Greene |
| 5,746,774 A | 5/1998 | Kramer et al. |
| 5,779,735 A | 7/1998 | Molino |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Connor |
| 6,007,582 A | 12/1999 | May |
| 6,113,642 A | 9/2000 | Petrofsky et al. |
| 6,206,932 B1 | 3/2001 | Johnson |
| 6,206,933 B1 | 3/2001 | Shorter et al. |
| 6,361,570 B1 | 3/2002 | Gow |
| 6,425,925 B1 | 7/2002 | Grundei |
| 6,494,039 B2 | 12/2002 | Pratt et al. |
| 6,517,585 B1 | 2/2003 | Le Moel et al. |
| 6,517,858 B1 | 2/2003 | Le Moel et al. |
| 6,610,101 B2 | 8/2003 | Herr et al. |
| 6,613,097 B1 | 9/2003 | Cooper |
| 6,645,252 B2 | 11/2003 | Asai et al. |
| 6,695,885 B2 | 2/2004 | Schulman et al. |
| 6,755,870 B1 | 6/2004 | Biedermann et al. |
| 6,764,520 B2 | 7/2004 | Deffenbaugh et al. |
| 6,955,692 B2 | 10/2005 | Grundai |
| 7,137,998 B2 | 11/2006 | Bedard et al. |
| 7,279,009 B2 | 10/2007 | Herr et al. |
| 7,313,463 B2 | 12/2007 | Herr et al. |
| 7,314,490 B2 | 1/2008 | Bedard et al. |
| 7,637,957 B2 | 12/2009 | Ragnarsdóttir et al. |
| 7,637,959 B2 | 12/2009 | Clausen et al. |
| 7,691,154 B2 | 4/2010 | Asgeirsson et al. |
| 7,736,394 B2 | 6/2010 | Bedard et al. |
| 7,799,091 B2 | 9/2010 | Herr et al. |
| 7,815,689 B2 | 10/2010 | Bedard et al. |
| 7,867,284 B2 | 1/2011 | Bedard |
| 2004/0064195 A1 | 4/2004 | Herr |
| 2006/0201757 A1 | 9/2006 | Dupuis et al. |
| 2006/0206043 A1 | 9/2006 | Yakimovich et al. |
| 2006/0249315 A1 | 11/2006 | Herr et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2008/0097269 A1 | 4/2008 | Weinberg et al. |
| 2010/0262260 A1 | 10/2010 | Bedard et al. |

FOREIGN PATENT DOCUMENTS

| | | |
|---|---|---|
| DE | 4229330 A1 | 3/1994 |
| EP | 0549855 A2 | 7/1993 |
| EP | 1166726 A1 | 1/2002 |
| EP | 1169982 A1 | 1/2002 |
| FR | 2623086 | 5/1989 |
| GB | 2201260 | 8/1988 |
| GB | 2 260 495 | 4/1993 |
| GB | 2 302 949 A | 2/1997 |
| JP | 59-32453 | 9/1985 |
| JP | 5-161668 | 6/1993 |
| JP | 11056885 | 3/1999 |
| JP | 2002-191654 A | 7/2002 |
| JP | 2002-219141 | 8/2002 |
| WO | WO 96/41599 | 12/1996 |
| WO | WO 99/08621 | 2/1999 |
| WO | WO 01/54630 | 8/2001 |
| WO | WO 01/72245 | 10/2001 |
| WO | WO 2005/087144 | 9/2005 |

OTHER PUBLICATIONS

Flowers et al., Journal of Biomedical Engineering: Transactions of the ASME; Feb. 1977, pp. 3-8.

FIG. 1

FIG_2

FIG_4

HIGH TORQUE ACTIVE MECHANISM FOR ORTHOTIC AND/OR PROSTHETIC DEVICES

FIELD OF THE INVENTION

The present invention relates to a joint actuation mechanism for orthotic and/or prosthetic devices. More particularly but not exclusive, the present invention relates to high torque active mechanism for orthotic and/or prosthetic devices.

BACKGROUND OF THE INVENTION

Many types of knee joints for orthotic and prosthetic devices are commonly available on the market. The most rudimentary joints do not allow knee flexion during active tasks such as walking and can be manually unlocked for tasks such as sitting. This type of joint does not help restore the natural dynamics of a healthy leg.

More advanced joints use mechanical design or electronic control allowing to automatically, albeit abruptly, switch between a locked state and an unlocked state of the knee hinge. This offers stability during the stance phase and flexion during the swing phase. However, because the transitions between the locked and unlocked states are not smoothly controlled, the natural dynamics of a healthy leg is not restored.

None of the commonly available orthosis knee joints on the market, and only a few prosthetic knees, allow the users to descend inclines and stairs because of the absence of controlled flexion during the stance phase.

Among the different technologies that are being used or could be used for actively controlling orthotic and prosthetic knee hinges, few are desirable. For example, an electric motor and gear set incorporated in an actuated hinge could provide the required torque and motion control, but is likely to be noisy, heavy and bulky.

Actuation systems incorporating controlled resistance hydraulic actuators such as the C-Leg® from Otto Bock have the ability to provide some level of motion control. However, these systems are difficult to package on orthotic devices due to the size of the components and to the mechanical arrangement of those parts on the leg support system.

Other technologies such as the active muscle assistance device developed by Tibion look promising. However, the motor requires a transmission system in order to provide the required torque and incorporating a transmission to the control system adds design complexity, weight and size to the solution.

The magnetorheological (MR) Damper technology utilized in the Rheo Knee™ from Ossur demonstrates excellent controllability and provides a good torque density, although not sufficient for an orthotic application.

Ideally, the actuation technology utilized on a controllable orthotic or prosthetic knee hinge would provide a good level of control and torque capacity while being light, compact, easy to integrate on the leg support system and operate silently.

Therefore there is a need for a controllable actuation system having high torque density, allowing a user to descend inclines stairs, while being compact enough to properly fitting on a leg support system.

OBJECTS OF THE INVENTION

Another object of the invention is to provide a high torque active mechanism for orthotic and/or prosthetic devices.

A further object of the invention is to provided a controllable actuation system having high torque density.

Yet another object of the invention to provide a controllable actuation system having high torque density allowing a user to descend inclines stairs, while being compact enough to properly fitting on a leg support system.

SUMMARY OF THE INVENTION

In accordance with an aspect of the present invention, there is provided an orthotic device for supporting a limb of a user, the orthotic device comprising: a proximal orthotic portion to be mounted to the proximal limb segment of the user; a distal orthotic portion to be mounted to the distal limb segment of the user; an orthotic joint portion interposed between the proximal and distal orthotic portions to be mounted to the joint of the user's limb for supporting the user's joint during flexion and extension thereof; a primary brake in operational communication with the orthotic joint portion for generating a braking force thereon during flexion and/or extension movements; and an additional frictional brake in operational communication with the primary brake and with the orthotic joint portion, wherein during flexion the primary brake causes the additional frictional brake to generate an additional frictional braking force on the joint portion.

In accordance with another aspect of the present invention, there is provided a prosthetic device for replacing the limb of a user, the prosthetic device comprising: at least one prosthetic portion; a prosthetic joint portion for being interposed between the prosthetic portion and another adjacent prosthetic portion or an adjacent limb segment of the user, the prosthetic joint portion providing the at least one prosthetic portion to pivot between flexion and extension movements relative to the another adjacent prosthetic portion or the adjacent limb segment of the user; a primary brake in operational communication with the prosthetic joint portion for generating a braking force thereon during flexion and/or extension movements; and an additional frictional brake in operational communication with the primary brake and with the prosthetic joint portion, wherein during flexion the primary brake causes the additional frictional brake to generate an additional frictional braking force on the prosthetic joint portion.

In accordance with a further aspect of the present invention, there is provided an orthotic/prosthetic device comprising: at least one device portion; a joint portion for providing for the at least one device portion to pivot between flexion and extension movements relative to another adjacent device portion or an adjacent limb segment of the user; a primary brake in operational communication with the joint portion for generating a braking force thereon during flexion and/or extension movements; and an additional frictional brake in operational communication with the primary brake and with the joint portion, wherein during flexion the primary brake causes the additional frictional brake to generate an additional frictional braking force on the joint portion.

In accordance with yet another aspect of the present invention, there is provided a frictional braking assembly for a prosthetic/orthotic device comprising a joint portion thereof comprising a rotating member for providing flexion and extension movement of the device and a primary brake in operational communication with the joint portion for generating a braking force thereon during flexion and/or extension movements; the assembly comprising: a frictional member for being mounted to the rotating member, the frictional member having a free end and another opposite end fixedly mountable to the joint portion; and a brake pad assembly for being placed in operational communication with the primary brake and the frictional member, wherein during flexion the primary brake acts on the brake pad assembly which in turn causes the frictional member to engage the rotating member and to provide an additional frictional braking force thereon.

In accordance with yet a further aspect of the present invention, there is provided an orthotic/prosthetic device comprising: at least one device portion; a joint portion for providing for the at least one device portion to pivot between flexion and extension movements relative to another adjacent device portion or an adjacent limb segment of the user; a brake in operational communication with the joint portion for generating a braking force thereon during flexion and/or extension movements; and a torque sensor comprising a deformable portion mounted to the joint portion and being in operational communication with the brake and a strain-sensor in operational communication with the deformable portion, wherein during braking the brake provides a braking torque which is transmitted to the deformable portion causing deformation thereof, said strain-sensor providing for measuring the deformation of the deformable portion thereby allowing for determining the torque.

In accordance with stilt another aspect of the present invention, there is provided a torque sensor for an orthotic/prosthetic device comprising a joint portion thereof for providing flexion and extension movement of the device and a brake in operational communication with the joint portion for generating a braking force thereon during flexion and/or extension movements, the torque sensor comprising: a deformable portion for being mounted to the joint portion and being put in operational communication with the brake; and a strain-sensor in operational communication with the deformable portion, wherein during braking the brake provides a braking torque which is transmitted to the deformable portion causing deformation thereof, the strain-sensor providing for measuring the deformation of the deformable portion thereby allowing for determining the torque.

In accordance with still a further aspect of the present invention, there is provided a brake pad lever for an orthotic/prosthetic joint device comprising a joint portion thereof for providing flexion and extension movement of the device, a primary brake for generating a braking force on the joint portion during flexion and/or extension movements and a pressure pad for applying pressure to the joint portion thereby generating an additional braking force thereon, the brake pad lever comprising: a deformable flexure portion for being put into contact with the joint portion; and a pad engaging portion for engaging the pressure pad and being mounted to the deformable flexure portion, wherein when the joint portion provides a flexion movement against the braking force of the primary brake, the joint portion so acts upon the deformable flexure as to cause the deformation thereof thereby causing the pad engaging portion to act on the pressure pad so as to apply pressure on the joint portion thereby generating an additional braking force thereon.

In accordance with yet another aspect of the present invention invention there is provided a joint actuator assembly for an orthotic and/or prosthetic joint, the joint actuator assembly comprising an MR damper to provide a controllable resistive torque on the axis of the orthotic and/or prosthetic joint and a friction brake mechanism in operational communication with the MR damper so as to be activated by the braking force generated by the MR damper thereby increasing torque density during braking.

In accordance with still yet another aspect of the invention, there is provided a knee joint actuator assembly for an orthotic and/or prosthetic knee joint, the knee joint actuator assembly comprising an MR damper to provide a controllable resistive torque on the axis of the orthotic and/or prosthetic knee joint and a friction brake mechanism in operational communication with the MR damper so as to be activated by the braking force generated by the MR damper thereby increasing torque density during braking.

In accordance with yet a further aspect of the present invention there is provided an orthotic joint comprising a joint actuator assembly comprising an MR damper to provide a controllable resistive torque on the axis of the orthotic joint and a friction brake mechanism in operational communication with the MR damper so as to be activated by the braking force generated by the MR damper thereby increasing torque density during braking.

In accordance with yet still another aspect of the present invention there is provided an orthotic knee joint comprising a knee joint actuator assembly comprising an MR damper to provide a controllable resistive torque on the axis of the orthotic knee joint and a friction brake mechanism in operational communication with the MR damper so as to be activated by the braking force generated by the MR damper thereby increasing torque density during braking.

In accordance with yet still a further aspect of the present invention there is provided a prosthetic joint comprising a joint actuator assembly comprising an MR damper to provide a controllable resistive torque on the axis of the prosthetic joint and a friction brake mechanism in operational communication with the MR damper so as to be activated by the braking force generated by the MR damper thereby increasing torque density during braking.

In accordance with still another aspect of the present invention there is provided an prosthetic knee joint comprising a knee joint actuator assembly comprising an MR damper to provide a controllable resistive torque on the axis of the prosthetic knee joint and a friction brake mechanism in operational communication with the MR damper so as to be activated by the braking force generated by the MR damper thereby increasing torque density during braking.

Other objects, advantages and features of the present invention will become more apparent upon reading of the following non-restrictive description of illustrative embodiments thereof, given by way of example only with reference to the accompanying drawings.

BRIEF DESCRIPTION OF THE FIGURES

Illustrative embodiments of the invention will be described by way of non-limiting examples only with reference to the accompanying drawings, in which like reference numerals indicate like elements throughout and in which.

DESCRIPTION OF THE ILLUSTRATIVE EMBODIMENTS

Generally stated, the present invention provides an orthotic/prosthetic device comprising at least one device portion (an orthotic portion or a prosthetic portion), a joint portion for providing for the at least one device portion to pivot between flexion and extension movements relative to another adjacent device portion or an adjacent limb segment of the user. A primary brake is in operational communication with the joint portion for generating a braking force thereon during flexion and/or extension movements. An additional frictional brake is in operational communication with both the primary brake and the joint portion. During flexion the primary brake causes the additional frictional brake to generate an additional frictional braking force on the joint portion.

Generally stated, a non-limitative illustrative embodiment of the present invention provides high torque active mechanism for an orthotic and/or prosthetic joint using a magnetorheological (MR) rotational damper incorporating a friction brake mechanism driven by the braking force generated by the MR damper. This combination of MR damper and friction brake mechanism allows an increase in torque density while keeping the same level of motion control offered by the MR damper alone.

The increased torque density achieved by this high torque active mechanism allows to minimize the size of the actuating system, i.e. its diameter and/or breath, while maximizing its braking torque capability. In this regard, the friction brake mechanism is advantageously positioned around the MR damper, such that the dimension of the package is minimized.

In the context of the forgoing description, "actuator" is used to describe a mechanical device for creating or controlling mechanical motion and as such the high torque active mechanism of the invention comprises an actuator or an actuation/actuator mechanism.

Figure 1:
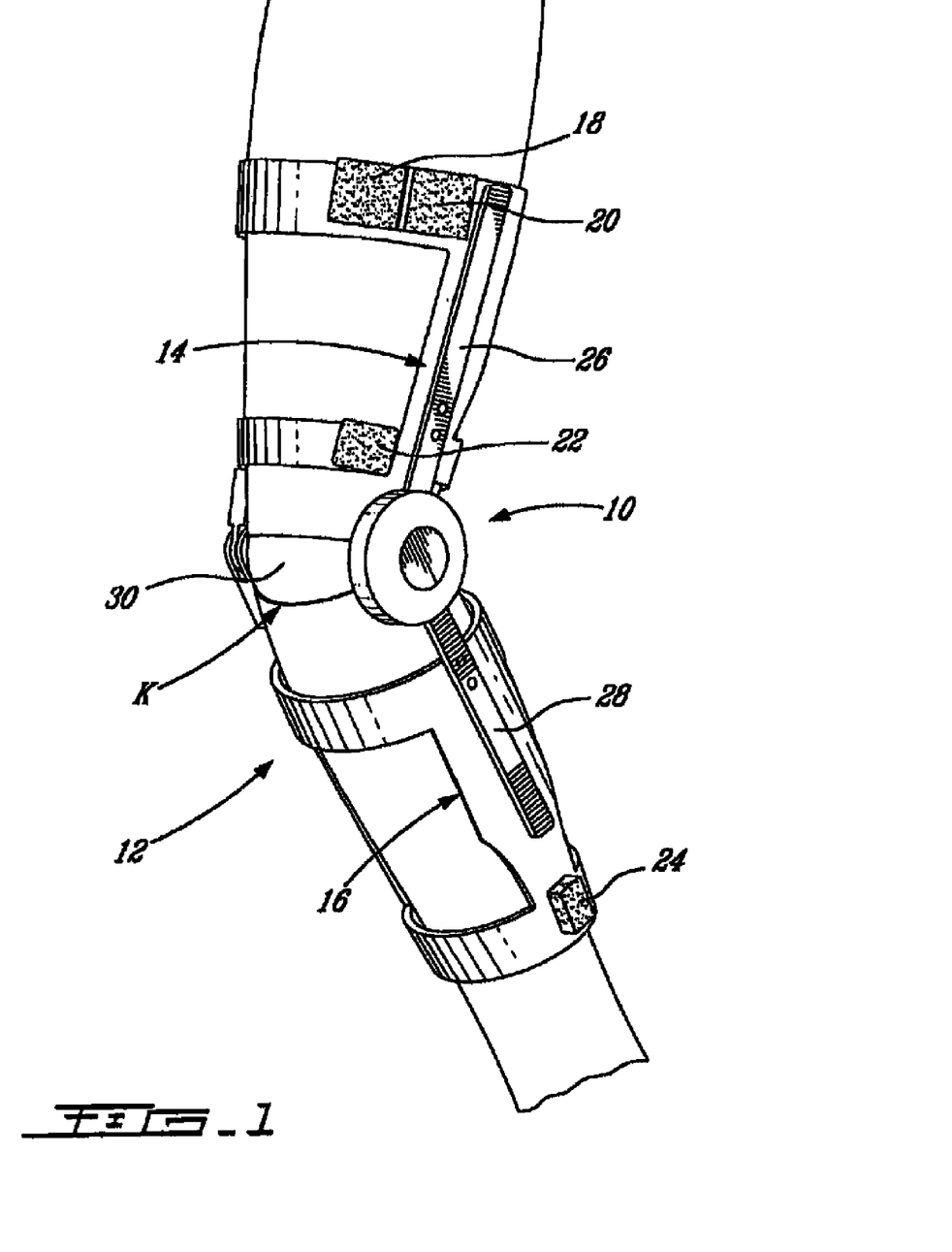
FIG. 1 is a perspective view of an actuated orthotic device in accordance with an illustrative embodiment of the present invention.

Referring to FIG. 1, there is shown a perspective view of the high torque active mechanism 10 applied to an actuated orthotic device 12.

The actuated orthotic device 12 generally comprises proximal (upper) 14 and distal (lower) 16 structural portions or shells and other components required for the control of the actuation mechanism such as, for example, a processing module 18, power management module 20, a power source 22, for example removable battery packs, integrated to the proximal orthotic shell 14 and a sensor module 24 integrated to the distal orthotic shell 12, feeding inertial data to the processing module 18.

The high torque active mechanism 10 may be mounted on the actuated orthotic device 12 on the lateral side of the user's knee K and is operationally connected between the proximolateral structural support 26 and the distolateral structural support 28 which form part of the proximal 14 and distal 16 portions respectively. A conventional hinge 30 may be used on the medial side, if required, to connect the proximal 14 and distal 16 portions or structural shells.

Figure 2:
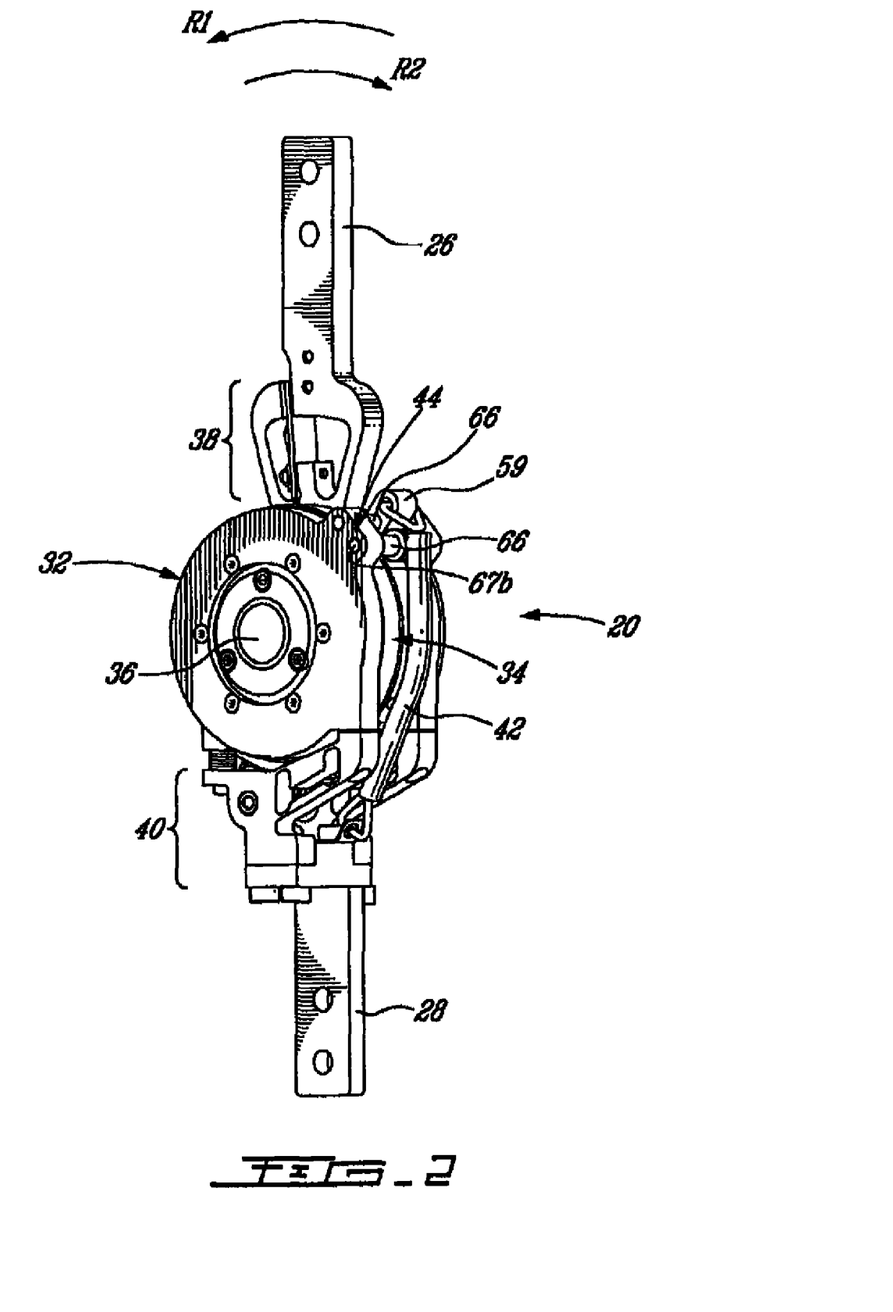
FIG. 2 is a perspective view of a high torque active mechanism according to the illustrative embodiment of the present invention.

Referring to FIG. 2, the high torque active mechanism 10 includes a joint portion in the form of a joint assembly 32 connecting the proximolateral 26 and the distolateral 28 structural supports. A magnetorheological (MR) rotational damper 34 is mounted to the joint assembly 32 and commands the braking torque provided by the high torque active mechanism 10. A rotational sensor 36 located on the MR damper 32 and measures the relative angle between the proximolateral 26 and the distolateral 28 structural supports. A torque sensor 38 is mounted on the proximolateral structural support 26 and the joint assembly 32 and measures the torque provided by the joint assembly 32. An additional frictional brake, namely braking mechanism 40 is mounted to the distolateral structural support 28 and the joint assembly 32 and is controlled by a primary brake, namely in this example, the braking torque provided by the MR damper 34 to augment the total braking capacity of the high torque active mechanism 10.

The joint assembly 32 includes an extension assist spring 42 to help the proximolateral 26 and the distolateral 28 structural supports get back in the extended position as well a rotational locking mechanism 44 which may be activated and deactivated by the user to manually block the high torque active mechanism 10, and consequently the actuated orthotic device 12, at a given angle. The rotational locking mechanism 44 may be, for example, a pin that may be inserted or removed to lock and unlock the rotor from the stator (both of which will be detailed further below).

Figure 3:
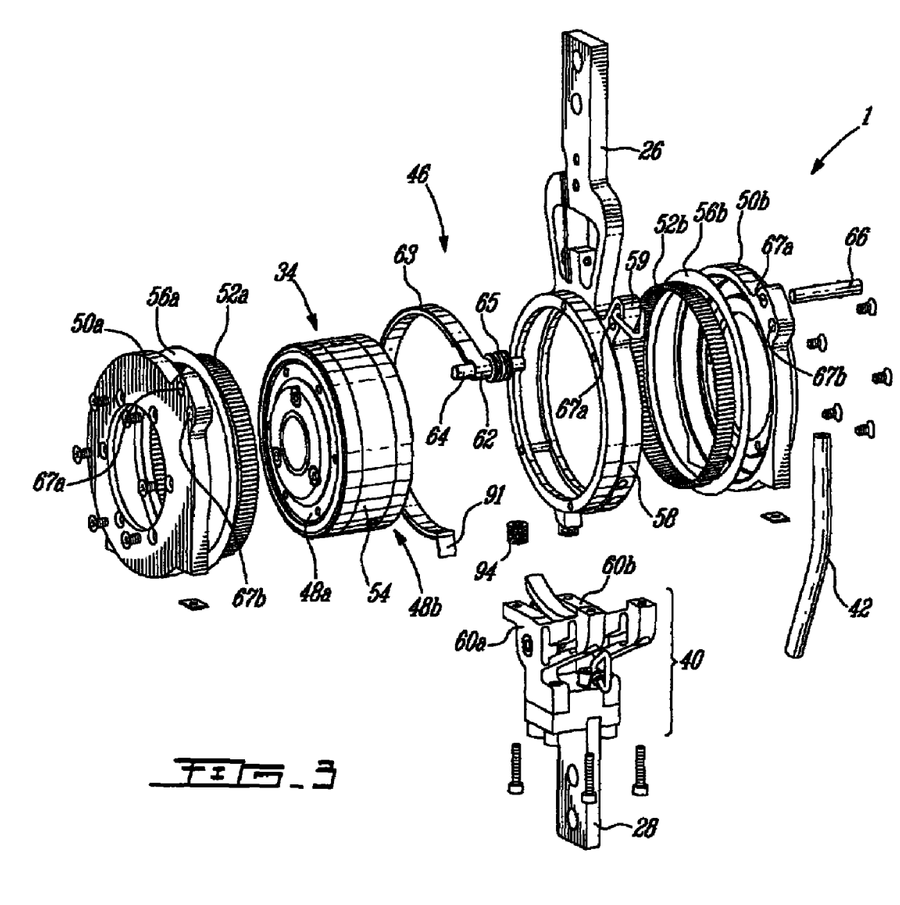
FIG. 3 is an exploded perspective view of the high torque active mechanism of FIG. 2.
Figure 5:
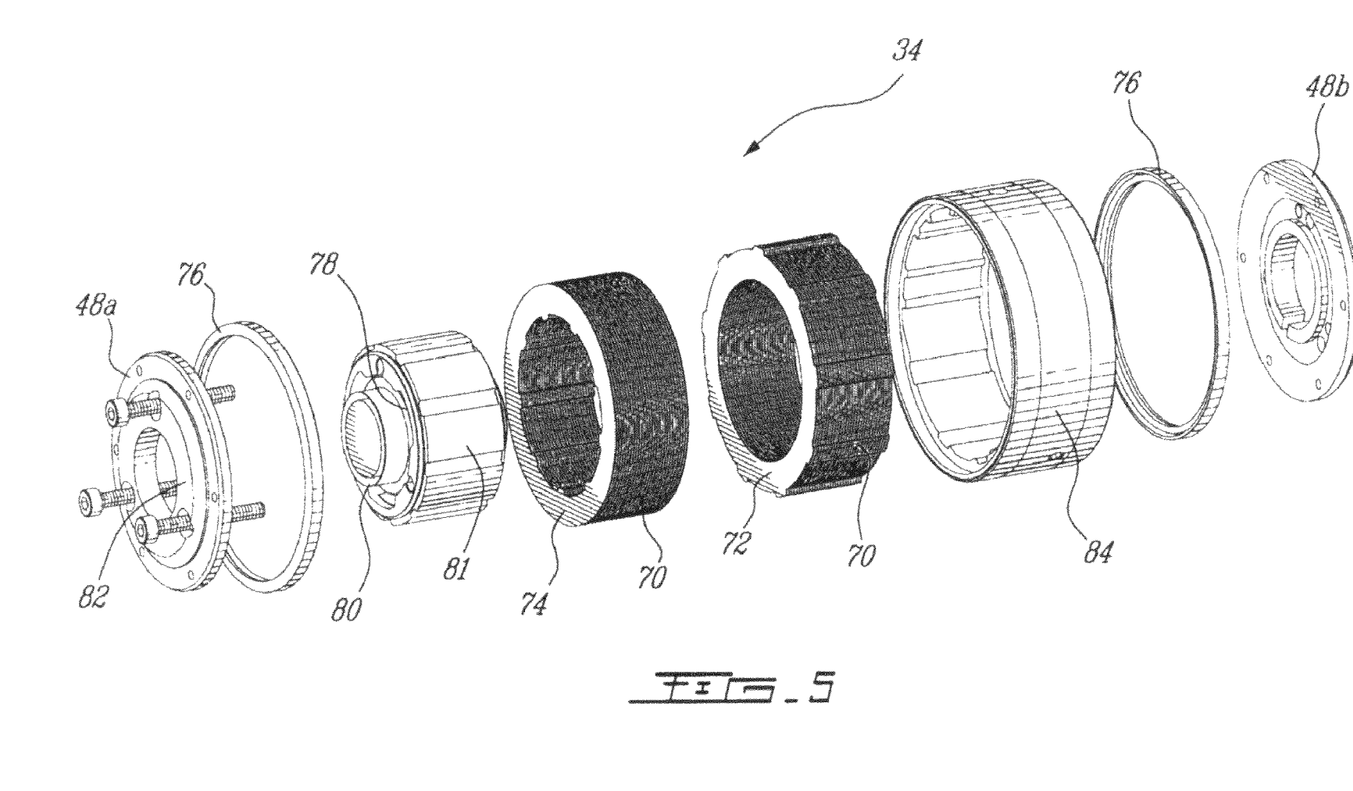
FIG. 5 is an exploded perspective view of the magnetorheological (MR) rotational damper of FIG. 4 in accordance with an illustrative embodiment thereof.

Referring now to FIG. 3, there is shown an exploded view of the complete joint assembly 32. As shown, the MR damper module 34 is surrounded by a frictional member in the form of a friction band brake mechanism 46 (also see FIG. 6) which is part of the additional frictional brake 40. Each side plate 48a and 48b (also see FIG. 5) of the MR Damper module is respectively attached to bearing covers 50a and 50b. The needle bearings sets 52a and 52b ensure radial positioning of the MR Damper rotor assembly (which as will be further discussed herein and as shown in FIG. 5 comprises cover plates 48a, 48b, rotor body 82, electromagnetic core 80, inductive coil 78, inner splines 81, and rotor blades 74) into the stator body 54, while trust washers 56a and 56b ensure axial positioning. The upper or proximolateral structural support 26 is permanently attached onto the stator body 54 via a rotating member in the form of a band brake drum 58. The lower or distolateral structural support 28 is attached to the bearing covers 50a and 50b through the brake pad levers 60a and 60b respectively. The friction band brake mechanism 46 comprises a frictional band 63. The fixed end 62 of the band 63 is secured to the bearing covers 50a and 50b with a retaining pin 64 through holes 67b. A locking pin 66 also allows to block the rotational movement between the upper or proximolateral structural support 26 and the bearing covers 50a and 50b when inserted in the holes 67a of covers 50a and 50b and of protuberance 59 of the band brake drum 58. A resilient flexible bumper 65 is mounted to the retaining pin 64.

MR Damper

Figure 4:
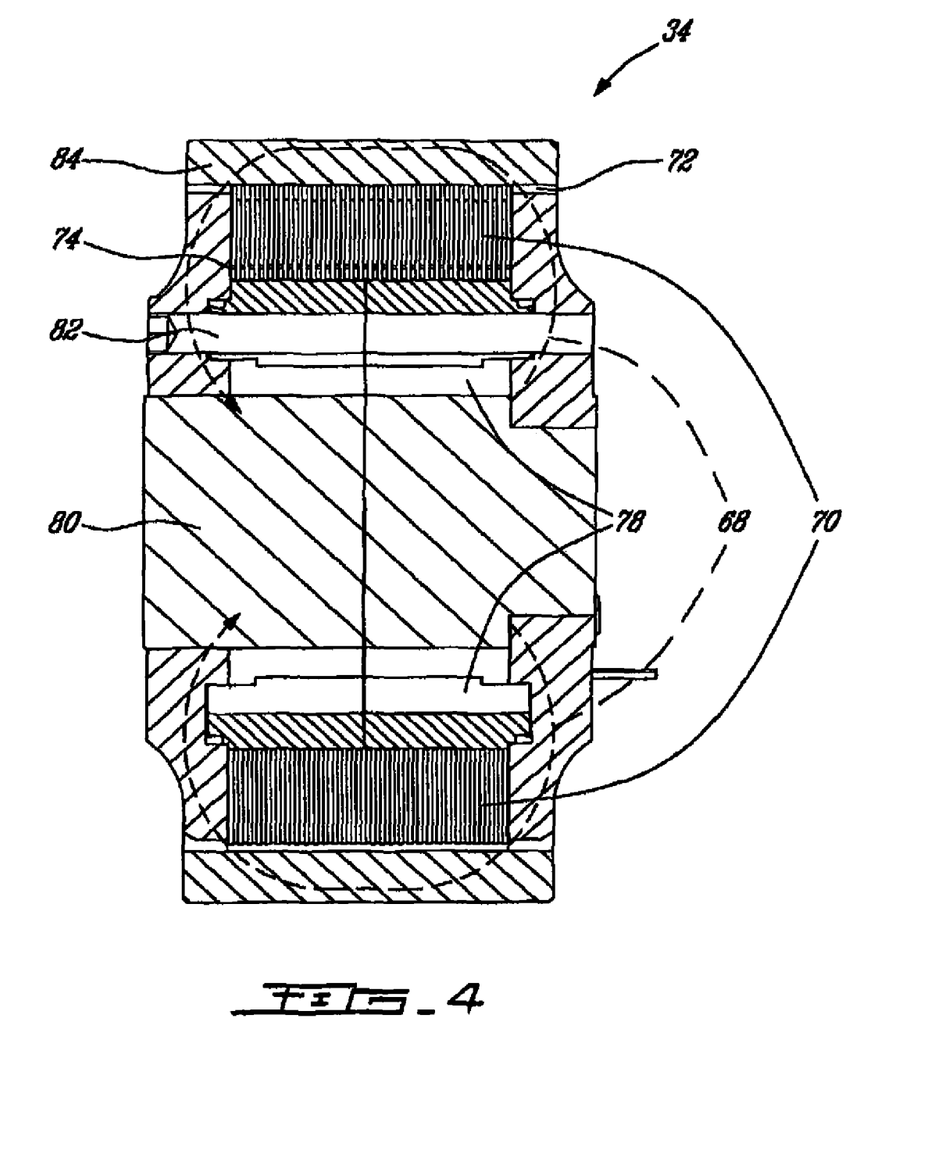
FIG. 4 is a cross-sectional view of a magnetorheological (MR) rotational damper of the high torque active mechanism of FIG. 2 in accordance with an illustrative embodiment thereof.

Referring to FIGS. 4 and 5, the controllable dissipative braking torque in the MR damper 34 is obtained by applying a magnetic field 68 through the magnetorheological fluid 70 occupying interstices between the stator blade array 72 and rotor blade array 74. The fluid 70 is sealed from the outside by rotational dynamic seals 76 (see FIG. 5). The magnetic field 68 can be dynamically controlled by regulating the current circulating in the inductive coil 78 winded around the electromagnetic core 80 within the inner spline 81. In the absence of a magnetic field 68, the magnetorheological fluid 70 viscosity is very low and the rotor body 82 is free to rotate inside the stator body 84. When the magnetic field increases, the fluid's ferromagnetic particles align with the magnetic field and created shear resistance between stator blades 72 and rotor blades 74, offering a breaking torque against applied moment through the knee joint.

As previously mentioned, for this invention, the MR damper 34 provides only a portion of the braking torque of the device: the friction brake provides the remaining braking torque. The main advantage of combining both braking technologies over a device comprised of only an MR damper is the greater torque density obtained without compromising the controllability. This results in a smaller package for a given braking torque capacity.

A non-limiting example of a MR damper 34 that may be used is described in U.S. Pat. No. 6,764,520 issues to Deffenbaugh et al. on Jul. 20, 2004 and incorporated herein by reference in its entirety. Of course, as the skilled artisan will readily understand a variety of MR dampers can be used and contemplated within the scope of the present invention.

Friction Band Brake Mechanism

Figure 6:
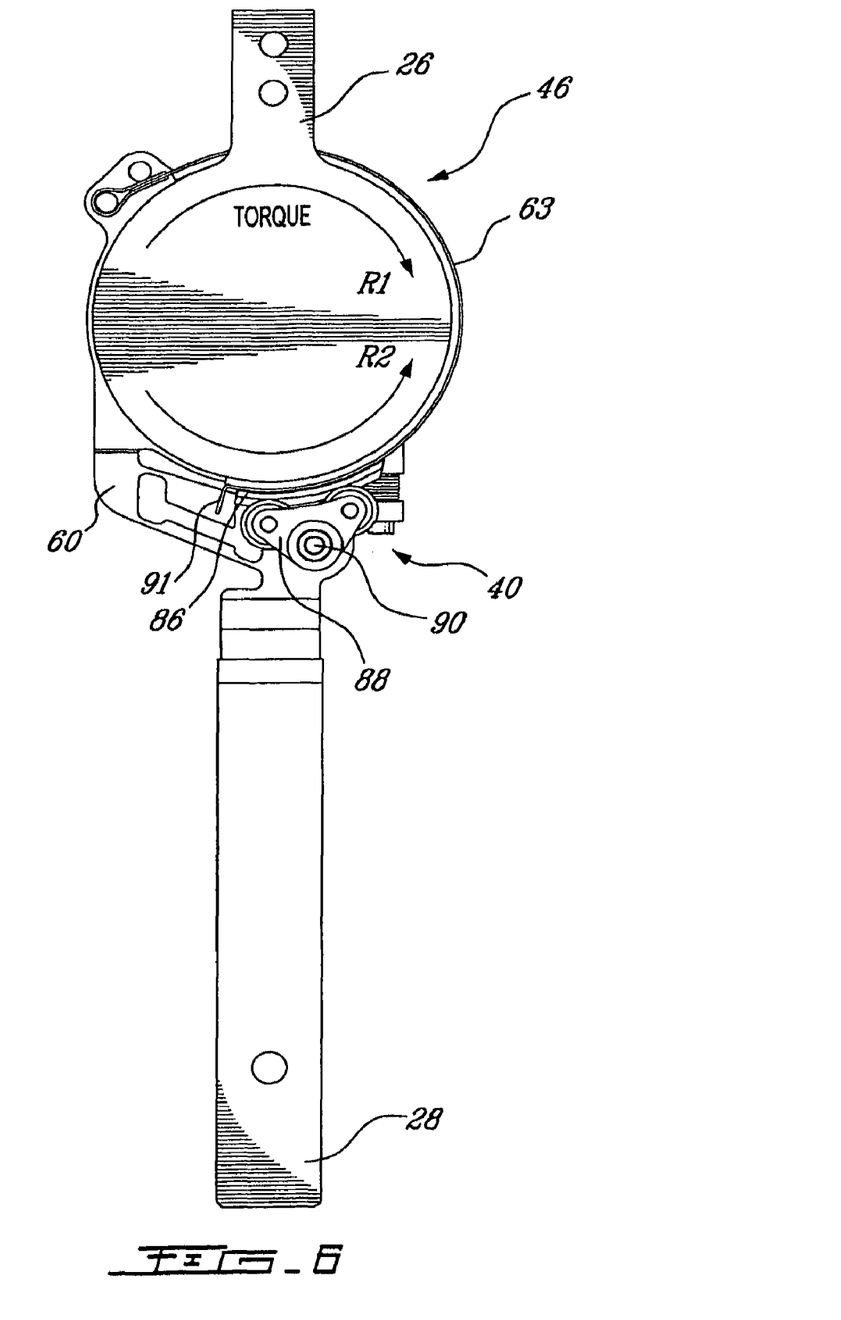
FIG. 6 is a lateral side view of the friction band brake mechanism of the high torque active mechanism of FIG. 2 in accordance with an illustrative embodiment thereof.

With reference to FIG. 6, the friction band brake mechanism 46 in accordance with an embodiment of the present invention will now be described.

Typically, a friction brake mechanism is complex to control and difficult to drive—as the contact forces required for the friction components are important relative to the size of the package. In the present invention, the friction band brake mechanism 46 is indirectly piloted by torque generated by the MR damper 34, which is easily and continuously controllable by regulating the current in the inductive coil.

In order to provide a compact package, the band-brake type braking system benefits of the substantially cylindrical configuration of the outer diameter of MR damper 34. The friction band brake mechanism 46 is piloted as follows: as the MR damper 34 provides a braking torque, this torque is transmitted to the brake pad lever, generally denoted 60, which basically transforms the torque into a pressure on the pressure pad 86 through a pressure pad engaging portion, namely a leveling system 88. The leveling system 88 is free to rotate around the leveling axis 90 and ensures that the pressure on the pressure pad 86 remains mostly even on its entire surface. The pressure pad 86 transmits the pressure to the free extremity 91, defining a downward flap, of the band 63. The other extremity 62 of the band 63 and the brake pad levers 60a and 60b (see FIG. 3) are connected to the lower or distolateral structural support 28 through the bearing covers 50a and 50b. More specifically, the fixed end 62 is mounted to the bearing covers 50a and 50b, via the retaining pin 64 which engages the respective holes 67b of the covers 50a and 50b. Furthermore, the covers 50a and 50b are also attached to the pad levers 60a and 60b which in turn are mounted to the lower or distolateral structural support 28.

In general, as the band brake drum 58 is also part of the upper structural support 26 as well as being part of the joint portion 32, the rotation of the upper structural support 26 creates a relative motion between the band 63 and the drum 58. If the rotation of the upper structural support occurs in the clockwise direction (R1 as viewed in FIG. 6 or FIG. 2) during flexion of the joint K, and if the MR damper 34 provides resistive torque, the free extremity 91 of the band 63 will be pulled in the R1 direction, activating this way the whole band brake mechanism 46 and creating an additional braking torque. A more detailed operation will be described further below.

The braking torque provided by the band brake mechanism 46 will be directly proportional to the torque of the MR Damper 34. The band brake mechanism 46 therefore acts as a torque multiplier for the MR Damper 34. The torque multiplication factor typically stands between 120% and 150%

It should be noted that the band brake mechanism 46 will not provide braking torque if the upper structural support 26 pivots or rotates in the counterclockwise or R2 direction, during extension of the joint K, because in this case the braking pad 86 as well as the free extremity 91 of the band brake 63 will be pulled away from the drum 58. In this case, only the MR Damper module 34 will provide braking torque.

The torque multiplication factor provided by the band brake mechanism 46 can be computed with the following information:

- the tension applied on the free extremity 91 of the band brake 63;
- the coefficient of friction of the band brake 63 surface with the drum 58; and
- the contact angle of the band brake 63.

The torque is computed using the following formulas:

$$M = (T_1 - T_2) \cdot R \quad (1)$$

and $$T_1 = T_2 \cdot e^{\mu \cdot \theta} \quad (2)$$

In this implementation of the band brake mechanism 46, the tension ($F_2$) applied on the free extremity 91 of the band 63 is a reaction to the pressure applied on the free extremity 91 of the band brake 63 by the pressure pad 86.

This pressure creates a friction force ($F_1$) that is computed with the force ($F_{pad}$) exerted by the pressure pad 86 and the coefficient of friction ($\mu$) of the band brake 63 on the drum 58.

$$T_2 = \mu \cdot F_{pad} \quad (3)$$

The force exerted on the pressure pad 86 depends on the geometry of the brake pad lever 60a and 60b and on the total torque exerted by the actuator 10 the relative to the knee joint K. The force can be computed with the following formula:

$$F_{pad} = \frac{T_{total}}{L_{lever}} \quad (4)$$

Where $T_{total}$ = Total torque of the actuator 10

$L_{lever}$ = Effective lever of the brake pad lever (60a or 60b, but can generally be denoted as 60 in FIGS. 6 to 9)

Brake Pad Lever

Figure 7:
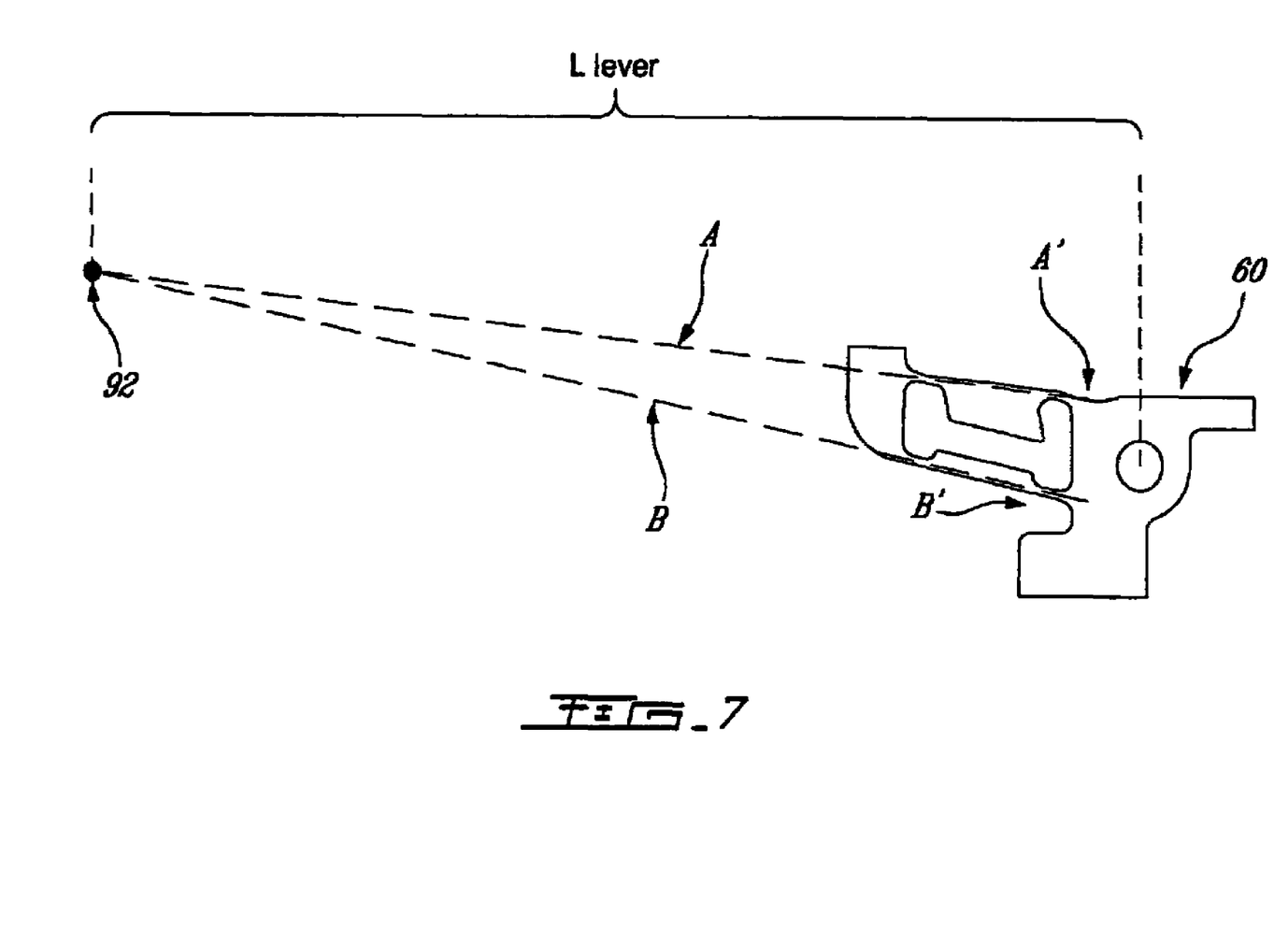
FIG. 7 is a lateral side view of the flexure mechanism of the friction band brake mechanism of FIG. 6 in accordance with an illustrative embodiment thereof.
Figure 8:
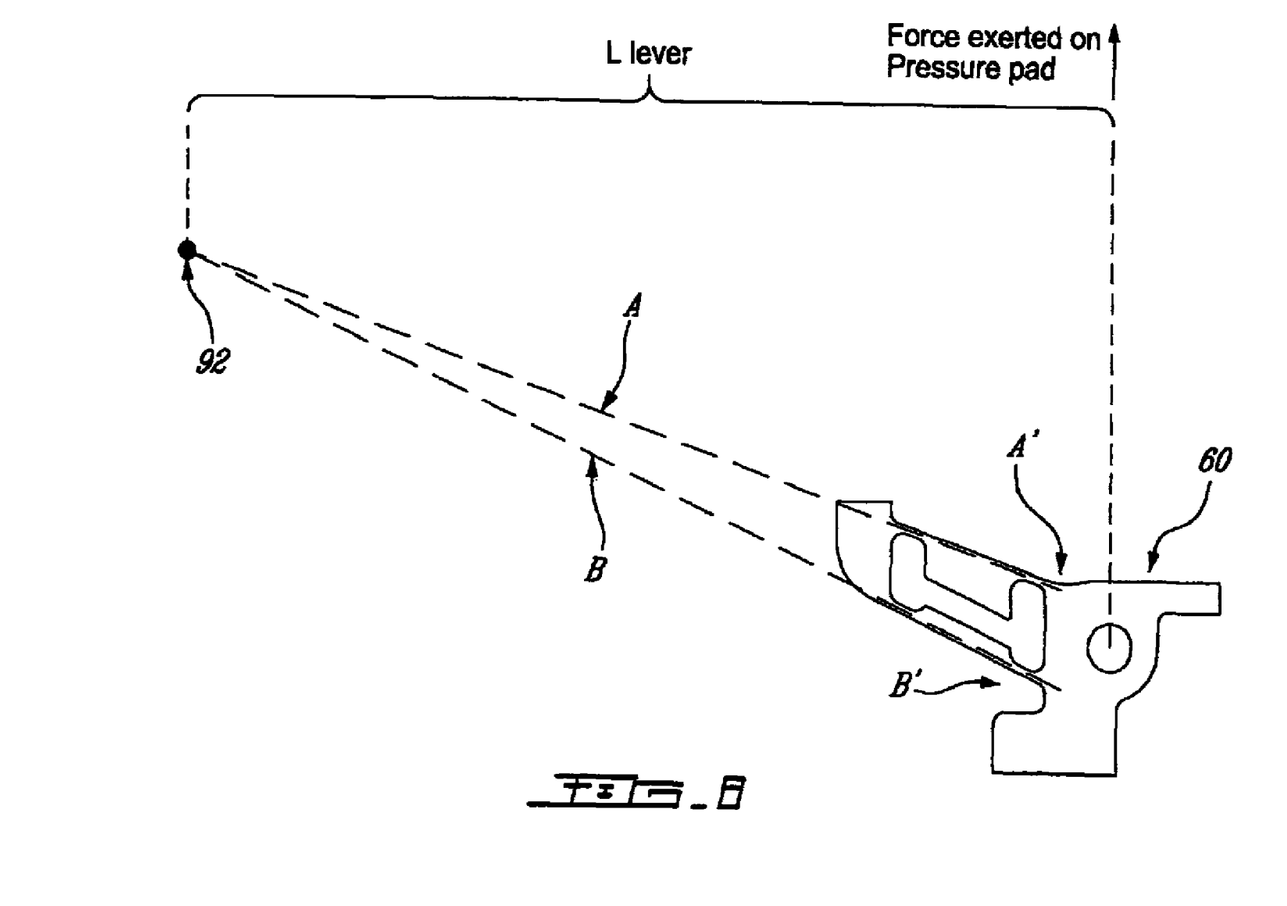
FIG. 8 is a lateral side view of the of the flexure mechanism of FIG. 7 in a deformed position.
Figure 9:
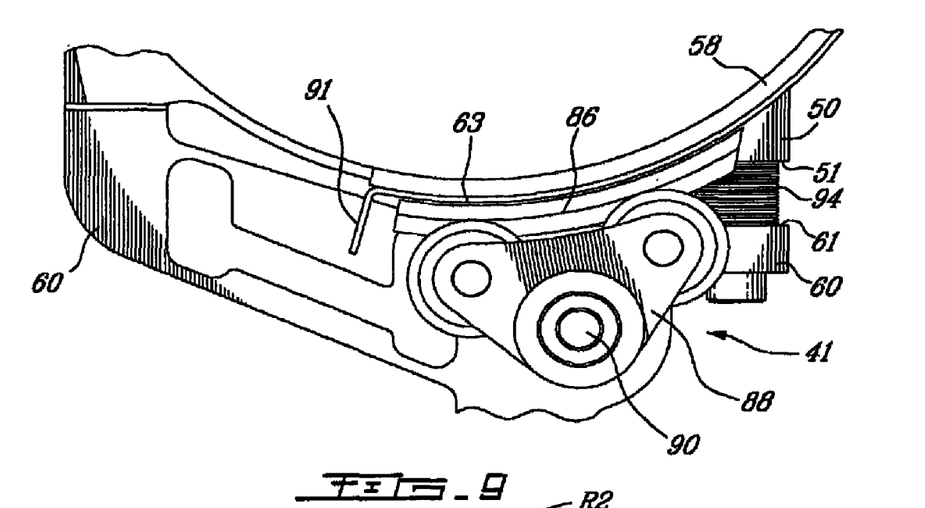
FIG. 9 is a lateral side view of the frictional braking mechanism of the friction band brake mechanism of FIG. 6 in accordance with an illustrative embodiment thereof.

With reference to FIGS. 7, 8 and 9, the brake pad lever 60 will be discussed in further detail.

In the present illustrative embodiment, the brake pad lever 60 is a flexure mechanism that provides a virtual pivot point 92. Another embodiment could include a standard rotational axis, such as a bearing. The virtual pivot point 92 provides to move the pivot point further away from the actuator mechanism 10, allowing extending the Effective Lever ($L_{lever}$), therefore reducing the pressure applied by the pressure pad 86.

The effective pivot point 92 of the flexure mechanism 60 is theoretically located at the intersection 92 of the lines A and B respectively created by the extension of the two flexures A' and B', as shown in the FIG. 7.

FIG. 8 shows deformed shape, which has been exaggerated here for descriptive purposes only, of the flexure mechanism 60 obtained by Finite Elements Analysis. This is valid for small deformations only, but in this application, the displacement will be very small considering that the gap between the pressure pad 86 and the band brake 63 is very small—in the order of 0.25 mm. It should be noted that at the lever length $L_{lever}$ remains basically the same than in FIG. 7.

With reference to FIG. 9, the brake pad lever 60 is that it is pushed away from the drum by a biasing member 94 in the form of a spring. Biasing spring 94 is mounted between a shoulder formed by the covers, generally denoted here by reference 50 and the shoulder 61 of the lever 60. The spring 94 ensures that the pressure pad 86 does not apply pressure on the band brake 63 when it is not desirable. In fact, one of the design criteria for the actuator 10 of the present invention is to maintain a high ratio between the maximum torque provided and the drag torque when the actuator 10 freely rotates. For that reason, it is desirable to ensure that the pressure pad 86 does not apply a pressure on the band brake 63 when the MR damper 32 is not activated. In fact, this situation normally happens when the joint K is in free swing (when the leg flexes and extends as the foot is not in contact with the ground). The spring 94 therefore provides the required force to maintain the pressure pad 86 away from the band brake 63 and drum 58 when the MR damper 34 is deactivated and while the joint K is moving in free swing (typically, the spring 94 provides the required force to oppose the drag torque of the MR Damper 34 at a maximum rotational speed of 360 deg/s).

A screw (not shown) coaxial to the spring 94 maintains the spring 94 pre-compressed to the desired force and maintains the brake pad lever 60 at the desired distance from the drum 58. It is important to so minimize the total gap between the pressure pad 86 and the drum 58, such that the user will not feel a step in the braking resistance when the band brake 56 engages. The aforementioned screw is also utilized to adjust this gap as the friction material wears.

Torque Sensor

Figure 10:
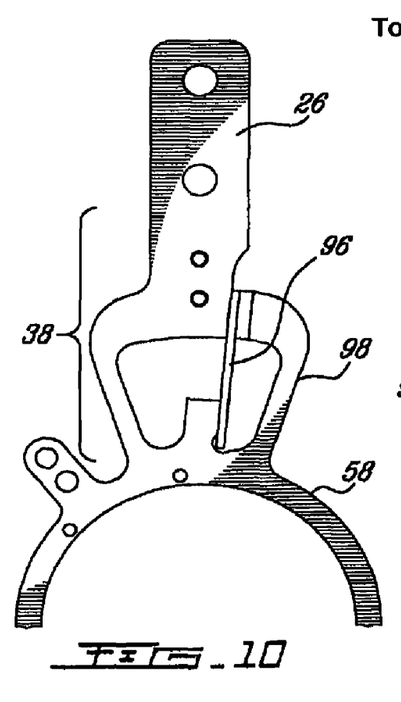
FIG. 10 is a lateral side view of the torque sensor of the high torque active mechanism of FIG. 2 in a accordance with an illustrative embodiment thereof.
Figure 11:
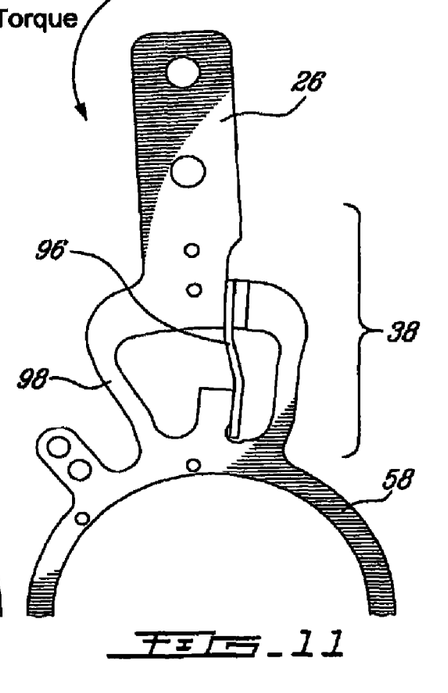
FIG. 11 is a lateral side view of the torque sensor of the high torque active mechanism of FIG. 10 in a deformed position.

The torque provided by the hybrid actuator 10 is directly measured using a torque sensing module 38 as displayed in FIG. 10. The torque sensor 38 comprises a deformable strip 96 inserted into a deformable frame 98. The braking torque of the actuator 10 is transmitted through the deformable frame 98 and causes the frame 98 to deform slightly. FIG. 11 shows an exaggerated deformation of the torque sensor 38: The deformable strip 96 is affected by the shape change of the frame 98 and deforms also in a generally S-shaped curve. Strain gages (not shown) are placed on the deformable strip 96 allow measuring the deformation and it is possible to compute the torque based on the measured deformation.

Of course, as the skilled artisan will readily comprehend other implementations for measuring the torque are possible, such as measuring the tension of the band 63 through strain gages or through the measured deformation of a spring on which the band 63 would be attached to give but two examples.

For clarity purposes only, it should be noted that the additional frictional brake, which was exemplified in the form of a frictional braking mechanism 40, also provides a frictional braking assembly comprising both the frictional band brake mechanism 46 (having band 63) and a brake pad assembly which includes the band brake lever 60 as well as the pressure pad 86.

Operation of the High Torque Mechanism 10

In operation, during rotation of the drum 58 (along with the upper structure 26), in the clockwise direction R1 (flexion of joint K) about the stator body 54 via the bearing 52a and 52b and between the fixed covers 50a and 50b. As the drum 58 rotates, the MR damper 34, when activated, will begin to resist and progressively break the rotational movement thereof. As the user goes beyond the foregoing resistive force or breaking force, this additional force (for moving drum 58 along with structure 26 in the R1 direction) deforms the break pad lever 60 (as represented in FIG. 8). As the lever 60 deforms, it is brought closer to the drum 58, thereby pushing the breaking pad 86 onto the band 63 and thereby pushing the band 63 onto the drum 58. Thereby, causing the band 63 to rotate or to be trained along with the drum 58 in the R1 direction as it is lead by the free end 91. Since the fixed end 62 of the band is anchored in position as described above, the trained band 63 is progressively strained or stretched as the free end 91 progressive moves in the R1 direction, this tension frictionally breaks the rotating movement of the drum 58.

When rotating the drum 58 in the counterclockwise direction (R2 in FIGS. 2 and 6), the lever 60 returns to its normal or non-deformed shape (see FIG. 7) moving away from the drum 58. Thereby, releasing the breaking pad 86 from being pushed onto the band 63, hence releasing the straining force on the band 63 and as such releasing the frictional force on the drum 58. The drum 58 continues to rotate in the R2 direction until its protuberance 59 engages the in resilient flexible bumper 65 that is fixedly mounted to retaining pin 66. Retaining pin 66 and bumper 65 therefore act as a stopper, the resilient and flexible bumper 65 provides for a cushioned stop.

It should be noted that although not illustrated, the high torque active mechanism can be applied to an actuated prosthetic device in accordance with the present invention.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described by way of particular embodiments and examples thereof, it should be noted that it will be apparent to persons skilled in the art that modifications may be applied to the present particular embodiment without departing from the scope of the present invention.

What is claimed is:

1. An orthotic device for a supporting a limb of a user, said orthotic device comprising:
    a proximal orthotic portion to be mounted to the proximal limb segment of the user;
    a distal orthotic portion to be mounted to the distal limb segment of the user;
    an orthotic joint portion interposed between said proximal and distal orthotic portions to be mounted to the joint of the user's limb for supporting the user's joint during flexion and extension thereof;
    a primary brake in operational communication with said orthotic joint portion for generating a braking force thereon during flexion and/or extension movements; and
    an additional frictional brake in operational communication with said primary brake and with said orthotic joint portion,
    wherein during flexion said primary brake causes said additional frictional brake to generate an additional frictional braking force on said joint portion.

2. An orthotic device according to claim 1, wherein said joint portion comprises a rotating member, said rotating member being rotatable in a respective direction during extension and flexion, said additional frictional brake comprising a frictional braking member for frictionally engaging said rotating member during braking.

3. An orthotic device according to claim 2, wherein said additional frictional brake comprises a brake pad assembly.

4. An orthotic device according to claim 3, wherein said brake pad assembly comprises a brake pad lever, said brake pad lever providing when acted upon by said rotating member to cause said brake pad assembly to engage and push said frictional member onto said rotating member.

5. An orthotic device according to claim 4, wherein said brake pad assembly comprises a leveling system so positioned as to provide said brake pad lever to act on said pressure pad via said leveling system.

6. An orthotic device according to claim 5, wherein said leveling system is pivotally mounted on said brake pad lever.

7. An orthotic device according to claim 5, wherein said primary brake provides a braking torque, said brake pad lever providing for transforming the braking torque into a pressure onto said pressure pad via said leveling system.

8. An orthotic device according to claim 4, wherein said brake pad assembly comprises a pressure pad, said brake pad lever so acting on said pressure pad when deformed as to cause said pressure pad to engage and push said frictional member onto said rotating member.

9. An orthotic device according to claim 8, wherein said primary brake provides a braking torque, said brake pad lever providing for transforming the braking torque into a pressure onto said pressure pad.

10. An orthotic device according to claim 4, wherein said brake pad lever is biased away from said rotating member via a biasing member.

11. An orthotic device according to claim 4, wherein said brake pad lever is so deformable by said rotating member as to cause said brake pad assembly to engage and push said frictional member onto said rotating member.

12. An orthotic device according to claim 4, wherein when acted upon by said rotating member said brake pad lever is so pivotable as to cause said brake pad assembly to engage and push said frictional member onto said rotating member.

13. An orthotic device according to claim 3, wherein said brake pad assembly is mounted to said distal orthotic portion.

14. An orthotic device according to claim 13, wherein said brake pad assembly is mounted to said distal orthotic portion via a distal support.

15. An orthotic device according to claim 3, wherein said brake pad assembly is in operational communication with said rotating member and with said frictional member, wherein during flexion when said rotating member rotates against the braking force of said primary brake, said rotating member so acts upon said brake pad assembly as to cause said brake pad assembly to engage and push said frictional member onto said rotating member.

16. An orthotic device according to claim 15, wherein said frictional member comprises a fixed end and an opposite free end, when said brake pad engages and pushes said frictional member onto said rotating member, said free end is trained along with said rotating member during rotation thereof thereby straining said frictional member onto said rotating member for frictional braking thereof.

17. An orthotic device according to claim 2, wherein said rotating member is mounted to said proximal orthotic portion.

18. An orthotic device according to claim 17, wherein said rotating member is mounted to said proximal orthotic portion via a torque sensor.

19. An orthotic device according to claim 18, wherein said torque sensor comprises a deformable strip mounted within a deformable frame.

20. An orthotic device according to claim 19, wherein said primary brake provides a braking torque which is transmitted to said deformable strip via said deformable frame.

21. An orthotic device according to claim 20, wherein strain gages provide for measuring the deformation of said deformable strip thereby allowing for determining the torque.

22. An orthotic device according to claim 17, wherein said rotating member is mounted to said proximal orthotic portion via a proximal support.

23. An orthotic device according to claim 22, wherein said rotating member is mounted to said proximal support via a torque sensor.

24. An orthotic device according to claim 2, wherein said frictional braking member comprises a frictional band mounted about said rotating member.

25. An orthotic device according to claim 24, wherein said frictional band comprises a fixed end and an opposite fee end.

26. An orthotic device according to claim 25, wherein said opposite free end is trained along with said rotating member during flexion thereby straining said frictional band onto said rotating member for frictional braking thereof.

27. An orthotic device according to claim 2, wherein said rotating member comprises a rotating drum.

28. An orthotic device according to claim 1, wherein said primary brake provides a braking torque, said additional frictional brake providing for transforming the braking torque into a pressure onto said joint portion thereby allowing frictional braking thereof.

29. An orthotic device according to claim 1, wherein said joint portion further comprises an MR damper, said MR damper providing for said primary brake.

30. An orthotic device according to claim 1, wherein said joint portion further comprises an actuator selected from the group consisting of a mechanical actuator, a hydraulic actuator, an electric actuator, a pneumatic actuator, an MR damper and a combination thereof.

31. An orthotic device according to claim 1, wherein said orthotic device is selected from the group consisting of a knee joint orthotic device and an ankle joint orthotic device.

32. An orthotic/prosthetic device comprising:
at least one device portion;
a joint portion for providing for said at least one device portion to pivot between flexion and extension movements relative to another adjacent device portion or an adjacent limb segment of the user;
a primary brake in operational communication with said joint portion for generating a braking force thereon during flexion and/or extension movements; and
an additional frictional brake in operational communication with said primary brake and with said joint portion, wherein during flexion said primary brake causes said additional frictional brake to generate an additional frictional braking force on said joint portion.

* * * * *

UNITED STATES PATENT AND TRADEMARK OFFICE
CERTIFICATE OF CORRECTION

| | |
|---|---|
| PATENT NO. | : 8,211,042 B2 |
| APPLICATION NO. | : 12/160736 |
| DATED | : July 3, 2012 |
| INVENTOR(S) | : Benoit Gilbert and David Landry |

It is certified that error appears in the above-identified patent and that said Letters Patent is hereby corrected as shown below:

On the Title page:
Item (73) Assignee on Page 1, Line 1, please change "Victom" to --Victhom--, therefor.

Item (57) Abstract on Page 1, Line 3, please change "provide" to --provided--, therefor.

Item (57) Abstract on Page 1, Line 5, after "incorporating", please delete "and".

Item (57) Abstract on Page 1, Line 12, please change "breath," to --breadth,--, therefor.

Item (56) References Cited on page 2, in Column 1, Line 35, under U.S. Patent Documents, change "Le Moel" to --Zahedi--, therefor.

In the Specification:
In Column 3, Line 22, please change "stilt" to --still--, therefor.

In Column 3, Line 56, after "invention", please delete "invention". (Second Occurrence).

In Column 5, Line 42, please change "breath," to --breadth,--, therefor.

In Column 8, Line 5, please change "150%" to --150%.--, therefor.

In Column 8, Line 31-33 (approx.), please delete "This...58." and insert the same after "86." on Col. 8, Line 30, as a continuation of the paragraph.

In Column 10, Line 21, after "the", please delete "in".

In the Claims:
In Column 10, Line 43, in claim 1, after "for", please delete "a".

Signed and Sealed this
Thirtieth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,211,042 B2  
APPLICATION NO. : 12/160736  
DATED : July 3, 2012  
INVENTOR(S) : Benoit Gilbert et al.

It is certified that error appears in the above-identified patent and that said Letters Patent is hereby corrected as shown below:

In the Claims

In Column 10, Line 45, please change "mounted to the" to --mounted to a--, therefor.

In Column 10, Line 47, please change "mounted to the" to --mounted to a--, therefor.

In Column 11, Line 5, please change "lever providing when acted upon by said rotating member" to --lever, when acted upon by said rotating member,--, therefor.

In Column 11, Line 6, please change "to cause said brake pad" to --causing said brake pad--, therefor.

In Column 11, Lines 9-10, please change "so positioned" to --positioned so--, therefor.

In Column 11, Lines 20-21, please change "lever so acting on said pressure pad when deformed" to --lever acting on said pressure pad when deformed so--, therefor.

In Column 12, Line 37, please delete "for" after "MR damper providing".

In Column 12, Line 50, please change "segment of the user" to --segment of a user--, therefor.

Signed and Sealed this  
Twenty-third Day of June, 2015

Michelle K. Lee  
*Director of the United States Patent and Trademark Office*